United States Patent [19]
Boyd

[11] Patent Number: 5,085,584
[45] Date of Patent: Feb. 4, 1992

[54] INTRAORAL DISCLUDER DEVICE AND METHOD

[76] Inventor: James P. Boyd, 9355 Vervain St., San Diego, Calif. 92129

[21] Appl. No.: 723,900

[22] Filed: Jul. 1, 1991

[51] Int. Cl.⁵ .............................................. A61C 3/00
[52] U.S. Cl. ........................................ 433/6; 433/215
[58] Field of Search ................ 433/6, 7, 215; 128/861

[56] References Cited

U.S. PATENT DOCUMENTS

| | | | |
|---|---|---|---|
| 3,513,838 | 5/1970 | Foderick et al. | 128/861 |
| 4,211,008 | 7/1980 | Lerman | 433/6 |
| 4,468,196 | 8/1984 | Keller | 433/7 |
| 4,559,013 | 12/1985 | Amstutz et al. | 433/8 |
| 4,773,853 | 9/1988 | Kussick | 433/6 |
| 4,798,534 | 1/1989 | Breads | 433/6 |
| 4,915,630 | 4/1990 | Honig | 433/215 |
| 4,920,984 | 5/1990 | Furumichi et al. | 433/6 |
| 4,997,182 | 3/1991 | Kussick | 128/861 |

*Primary Examiner*—John J. Wilson
*Attorney, Agent, or Firm*—Frank D. Gilliam

[57] ABSTRACT

An intraoral discluding device for the prevention of chronic tension and common migraine headaches and temporal-mandibular joint syndrome that are caused by chronic clenching of the posterior mandibular and maxillary teeth by the temporalis muscle. The discluder is a small intraoral device which is custom made for the individual. The device includes a small, typically acrylic, dome-shaped tab supported by a conventional palatal member which is retained by bent orthodontic wire. The device is inserted in the mouth and retained against the upper anterior teeth with the tab extending such that as the mouth is closed the tab will come into contact with the lower anterior incisal edges before the posterior teeth can touch each other. This renders the temporalis muscles ineffective, preventing high pressure clenching of the posterior teeth. While the device may be worn most of the time, including during sleep, it is not attached permanently and is always removed for eating, which prevents super eruption of the teeth.

6 Claims, 1 Drawing Sheet

INTRAORAL DISCLUDER DEVICE AND METHOD

BACKGROUND OF THE INVENTION

This invention relates in general to the prevention of tension and common migraine headaches and temporal mandibular syndrome and, more specifically, to an intraoral device for preventing those conditions.

Many people suffer from recurring tension, or muscle contraction, headaches ranging from mild to severe. The severity of the headache often mimics the severity of classic migraine and can be diagnosed as "common migraine".

Tension is a muscular property. Muscles tense, or contract, to do work. When a muscle contracts statically and continually it will become painful. The intensity or degree of contraction and longevity of contraction will dictate the degree of discomfort.

The majority of the muscles that cover the human head (i.e., skull) are responsible for facial expression (raising eyebrows, smiling, etc.). Theses muscles are not strong enough to elicit the type of discomfort associated with headaches. There is an extremely powerful muscle, however, located on the side of the skull, extending from just behind the eye to just behind the ear. This muscle, the temporalis muscle, has one function to close (or "elevate") the lower jaw. When isometrically contracted, the temporalis muscle can exert a tremendous amount of static force. This isometric contraction can only occur when the posterior mandibular and maxillary teeth or dentures are in contact with each other.

The common tension headache in the temporal region is caused by moderate to severe inappropriate contraction of the temporalis muscles. Under usual and normal circumstances, the upper and lower teeth should rarely, if ever, come into pressure contact other than during normal chewing. The inappropriate muscular activity that clenches the upper and lower jaws together along with their associated dentition is called myofascial dysfunction.

Clenching is a motionless act, therefore, it is practically impossible to notice another person clenching. Additionally, clenching is most commonly done while the person is concentrating on another topic, or while dreaming, so that it is very difficult to have a self awareness of clenching.

As the muscular contraction condition of clenching continues, the muscles become fatigued and susceptible to spasm and cramping. The pain from a spasming or cramping temporalis muscle is quite severe and is usually diagnosed as "common" migraine. This type of migraine initiates as a severe headache that may last for two to three days. The muscle contraction headache patient, when seen by a physician, is usually treated with muscle relaxants and analgesics and may be referred to a physical therapist to treat the fatigued muscles. This treats the symptoms but does not address the cause.

These patients, when seen by a dentist, are commonly diagnosed as having temporal-mandibular joint syndrome. It is felt that a dysfunctional temporal-mandibular joint or an improper jaw-to-skull relationship causes the muscles to contract improperly, resulting in the headache. These patients are typically treated with a "jaw-repositioning" appliance, designed to relieve pressure on the distressed temporal-mandibular joint and allow a proper jaw-to-skull relationship. Typical of these are the orthotics or splints described by Norton in U.S. Pat. No. 4,671,766 and Sullivan in U.S. Pat. No. 4,519,386. The appliance, or splint, covers either the upper or lower posterior teeth and dictates jaw position by guiding the opposing jaw into "normal" position. Unfortunately, the upper and lower jaws are approximated by way of the splint, thus allowing the clenching to persist.

Thus, there is a continuing need for improved means and methods for preventing clenching of the teeth for prolonged periods to eliminate the resulting headaches and other related problems.

SUMMARY OF THE INVENTION

The above-noted problems, and others, are overcome in accordance with this invention by a small intraoral device that can be fitted to a patient's mouth to inhibit inappropriate isometric contraction of the temoporalis muscles. The device includes an orthodontic plate, similar to those used to support dentures, custom shaped to fit inside the patient's mouth, adjacent to the lingual surface of the upper maxillary anterior incisors. The plate includes a small tab or dome that extends such that as the jaws come together, the lower anterior incisal teeth edges come into contact with the dome before the upper and lower posterior teeth can touch each other. This maintains disclusion of the posterior teeth and prevents clenching. The dome should be positioned so that when in place disclusion is maintained in all excursive movements.

The plate is held in place in a conventional manner by bent orthodontic wire. Preferably, the plate extends transversely a sufficient distance across the anterior teeth such that the support wires are towards the side of the mouth and are inconspicuous.

The device should not be attached permanently, since it must be removed while eating. The device could be installed at all other times. In particular, it should be used during stressful activities and while sleeping.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
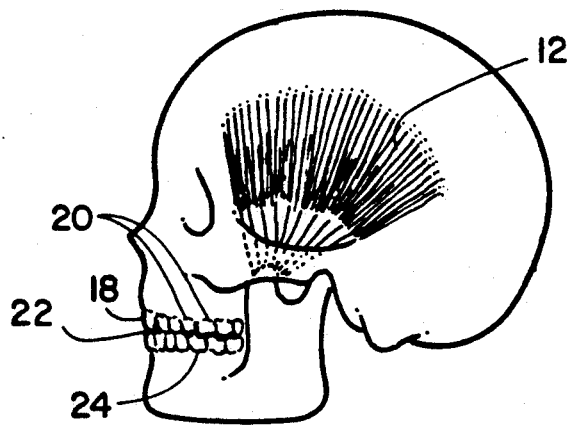
FIG. 1 is a schematic side elevation view of a human skull with the discluder device of this invention in use.

Referring now to FIG. 1, there is seen a schematic representation of a human skull 10. The temporalis muscle 12 extends from the skull to the jaw 14, with contraction of muscle 12 causing jay 14 to close. When the discluder 16 of this invention (as detailed in FIGS. 2-4) is in place along the anterior teeth 18 in FIG. 1, only the orthodontic wires 20 and, perhaps, the tip of dome 22 can be seen. As is apparent, the lower anterior teeth contact dome 22, preventing posterior teeth from coming into contact.

Figure 2:
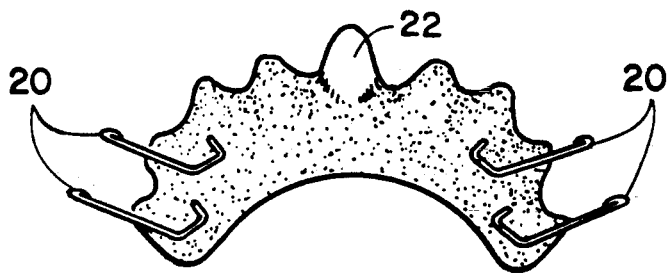
FIG. 2 is a plan view of the discluder device looking from below.
Figure 3:
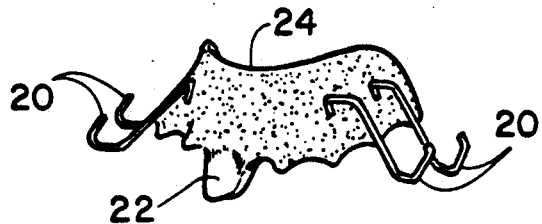
FIG. 3 is a perspective view of the discluder device.

The discluder 16 is shown in detail in FIGS. 2 and 3. It includes plate 26 which is typically formed from dental acrylic resin, orthodontic wires 20 embedded in plate 26 and bendable into the proper position for holding plate 26 in place against the anterior teeth and dome 22, which is also typically formed from acrylic material. Plate 24 conventionally has a pink, "gum colored", color, while dome 22 may be white to blend in with the teeth. For many patients, dome 22 need not extend below the upper anterior teeth, so as to be very inconspicuous. Plate 24 preferably is fairly wide, so that wires 20 engage teeth at the sides of the mouth and are unobtrusive.

Figure 4:
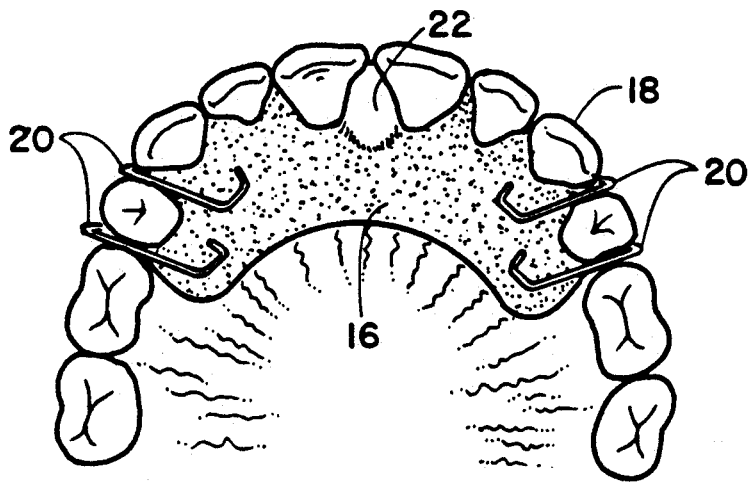
FIG. 4 is a plan view of the discluder device in place in a patient's mouth, looking from below.

FIG. 4, in a view looking up at the mouth interior, shows discluder 16 in place, with wires 20 engaging teeth to hold the discluder in place and dome 22 projecting downwardly adjacent to the incisors, where it will be contacted by lower incisors to prevent further closing of the jaw. Plate 16 and wires 20 are constructed and fitted in the same manner that conventional dentures are made and fitted.

Other applications, variations and ramifications of this invention will occur to those skilled in the art upon reading this disclosure. Those are intended to be included within the scope of this invention, as defined in the appended claims.

I claim:

1. An intraoral discluder device which comprises:
   a plate configured to lie adjacent to the interior surface of the upper anterior teeth of a patient;
   a dome on said plate adapted to extend toward the lower anterior teeth when said plate is in place in said patient's mouth;
   said dome configured to contact at least one lower anterior tooth when in place in said patient's mouth prior to any contact between the upper and lower posterior teeth; and
   at least one orthodontic wire means for securing said plate in place in said patient's mouth.

2. The device according to claim 1 wherein said plate and dome are fabricated from an acrylic resin.

3. The device according to claim 1 wherein said plate extends transverse to said anterior teeth and at least one orthodontic wire is located near each end of said plate and is adapted to secure said plate to teeth near the sides of the mouth.

4. The method of preventing the occurrence of chronic tension and common migraine headaches and temporal mandibular syndrome which comprises the steps of:
   providing a device comprising a plate configured to lie adjacent to the interior surface of the upper anterior teeth of a patient, said plate having a dome and at least one orthodontic wire;
   fitting said device to a patient's mouth and teeth configuration with said dome extending toward said lower anterior teeth such that said dome will contact at least one lower anterior tooth prior to any contact between posterior teeth and arranging said at least one orthodontic wire so as to hold said device in position;
   placing said device in the patient's mouth for selected periods; and
   removing said device when the patient is eating.

5. The method according to claim 4 wherein said plate and dome are fabricated from an acrylic resin.

6. The method according to claim 4 wherein said plate is placed transverse to said anterior teeth and at least one orthodontic wire is located near each end of said plate and is adapted to secure said plate to teeth near the sides of the mouth.

* * * * *